United States Patent
Jackson (10) Patent No.: US 12,350,409 B1
(45) Date of Patent: Jul. 8, 2025

(54) WIRELESSLY CONTROLLED HEAT, WIND, AND FRAGRANCE DIFFUSER SINGLE TOWER SYSTEM

(71) Applicant: Micah D'Artagnan Jackson, Windsor Hills, CA (US)

(72) Inventor: Micah D'Artagnan Jackson, Windsor Hills, CA (US)

( * ) Notice: Subject to any disclaimer, the term of this patent is extended or adjusted under 35 U.S.C. 154(b) by 845 days.

(21) Appl. No.: 17/148,422

(22) Filed: Jan. 13, 2021

Related U.S. Application Data (60) Provisional application No. 62/961,036, filed on Jan. 14, 2020.

(51) Int. Cl.
*A61L 9/12* (2006.01)
*A61L 9/03* (2006.01)
*G06F 3/04847* (2022.01)
*G06F 3/0488* (2022.01)
*G08C 17/02* (2006.01)
*G08C 23/04* (2006.01)

(52) U.S. Cl.
CPC .............. *A61L 9/122* (2013.01); *A61L 9/032* (2013.01); *G06F 3/04847* (2013.01); *G06F 3/0488* (2013.01); *G08C 17/02* (2013.01); *G08C 23/04* (2013.01); *A61L 2209/11* (2013.01); *A61L 2209/134* (2013.01); *G08C 2201/93* (2013.01)

(58) Field of Classification Search
CPC ...... A61L 9/122; A61L 9/032; A61L 2209/11; A61L 2209/134; G06F 3/04847; G06F 3/0488; G08C 17/02; G08C 23/04; G08C 2201/93
See application file for complete search history.

(56) References Cited

U.S. PATENT DOCUMENTS

| | | | |
|---|---|---|---|
| 4,791,251 A * | 12/1988 | Carter | A61L 9/12 222/638 |
| 10,873,190 B2 * | 12/2020 | Chien | F21V 33/0048 |
| 11,369,771 B2 * | 6/2022 | Lazarovich | A61B 5/0205 |
| 2010/0001648 A1 * | 1/2010 | De Clercq | H05B 45/20 315/294 |
| 2015/0305320 A1 * | 10/2015 | Hedman | A01M 1/24 43/132.1 |
| 2018/0021629 A1 * | 1/2018 | DeLuca | A63B 21/00069 482/4 |
| 2019/0267825 A1 * | 8/2019 | Chien | F21S 6/00 |
| 2020/0129727 A1 * | 4/2020 | Lazarovich | A61B 5/01 |
| 2020/0237297 A1 * | 7/2020 | Lazarovich | G16H 40/67 |

* cited by examiner

*Primary Examiner* — Regina M Yoo
(74) *Attorney, Agent, or Firm* — Plager Schack LLP; Mark H. Plager; Stephen Hallberg (57) ABSTRACT

A wirelessly controlled heat, wind, and fragrance diffuser single tower system is disclosed that combines three separate devices into one system which provides cooling air from a fan, warmth from a heating lamp or element, and fragrances from a fragrance diffuser. Moreover, these separate components are controlled by external software which works to combine the elements to produce specific desired effects. In this way, one could replicate the sensation of lounging on a beach by emitting a coconut fragrance, which is blown into the air by the fan, while the heating element provides direct heat, simulating the warmth of the sun. The careful timing and combination of these elements would be directed by software, which would send commands to the device via wireless communication (Bluetooth, WiFi, etc.).

14 Claims, 3 Drawing Sheets

WIRELESSLY CONTROLLED HEAT, WIND, AND FRAGRANCE DIFFUSER SINGLE TOWER SYSTEM

CLAIM OF BENEFIT TO PRIOR APPLICATION

This application claims benefit to U.S. Provisional Patent Application 62/961,036, entitled "WIRELESSLY CONTROLLED HEAT, WIND, AND FRAGRANCE DIFFUSER SYSTEM," filed Jan. 14, 2020. The U.S. Provisional Patent Applications 62/961,036 is incorporated herein by reference.

BACKGROUND

Embodiments of the invention described in this specification relate generally to local environment controllers, and more particularly, to a wirelessly controlled heat, wind, and fragrance diffuser single tower system that includes several integrated components configured to expel heat and produce wind/air flow via integrated fan (hot air and/or cool air), diffuse fragrances via fragrance diffuser, provide an interface for human interaction with the tower via integrated display, and programmatically run automated programs via a main control board, computing devices, and associated software in wireless connection with and controlled by a virtual reality ("VR") software program on a VR headset with radio hardware for wireless data communication with the tower when worn by a subject.

The combination of aromatherapy scents and fragrances and a controlled climate can induce a pleasurable atmosphere for relaxation and meditation. However, in order to strike the right balance between airflow and aroma, one would have to experiment with separate devices which may or may not complement each other. Also, finding a pleasurable temperature and climate for homes and dwellings is a common challenge, especially in certain spaces which may not have good circulation or air flow.

Fragrance diffusers typically have a single function of disbursing atomized essential oils into the air. Fans and heaters are typically separate devices, which are used independently to modify room temperatures. None of the existing devices combine all these aspects into a single system. Furthermore, these separate devices are rarely used simultaneously to create a specific, desired atmosphere. One reason this combination of devices is not used together is because it often requires too much effort from the user to properly set up and monitor the independent components.

Therefore, there is an unmet need to combine three separate devices into one system which provides cooling air from a fan, warmth from a heating lamp or heating element and fragrances from a fragrance diffuser, all of which are wirelessly controlled by external software which works to combine the elements to produce specific desired effects.

BRIEF DESCRIPTION

A novel wirelessly controlled heat, wind, and fragrance diffuser single tower system is disclosed. In some embodiments, the wirelessly controlled heat, wind, and fragrance diffuser single tower system includes a plurality of integrated components configured to expel heat and produce wind/air flow via integrated fan (hot air and/or cool air), diffuse fragrances via fragrance diffuser, provide an interface for human interaction with the tower via integrated display, and programmatically run automated programs via a main control board, computing devices, and associated software in wireless connection with and controlled by a VR software program running on a VR headset with radio hardware for wireless data communication with the tower when worn by a subject.

In some embodiments, the wirelessly controlled heat, wind, and fragrance diffuser single tower system combines the plurality of integrated components into a single tower. In some embodiments, the wirelessly controlled heat, wind, and fragrance diffuser single tower system includes a tower housing that houses and incorporates the plurality of integrated components. In some embodiments, the plurality of integrated components comprise three separate devices that are combined and integrated into the single tower (in tower housing) as an integrated system which provides cooling air from a fan, warmth from a heater, and fragrances from a fragrance diffuser. In some embodiments, the fragrance diffuser is an aromatherapy diffuser. In some embodiments, the fragrance diffuser is a waterless oil atomizer diffuser. In some embodiments, the wirelessly controlled heat, wind, and fragrance diffuser single tower system includes a fragrance storage location in which one or more containers of fragrance or scent are stored for later use with the fragrance diffuser. In some embodiments, the fan is an oscillation cooling fan. In some embodiments, the oscillation cooling fan is configured to distribute cool air. In some embodiments, the oscillation cooling fan is configured to distribute scent and fragrances from the aromatherapy diffuser. In some embodiments, the oscillation cooling fan is configured to simultaneously distribute both cool air and scents and fragrances from the aromatherapy diffuser. In some embodiments, the oscillation cooling fan is configured to operate at a fan oscillation speed specified by the VR software program from among a plurality of fan oscillation speeds. In some embodiments, the heater comprises a heating component and a heat distribution fan. In some embodiments, the heating component comprises a heating coil. In some embodiments, the heating component comprises a heating lamp. In some embodiments, the heating lamp is an infrared heating lamp. In some embodiments, the heat distribution fan is configured to operate at a heater fan speed specified by the VR software program from among a plurality of heater fan speeds.

In some embodiments, the wirelessly controlled heat, wind, and fragrance diffuser single tower system includes a main control board, a touchscreen display, a computing device, and a program which runs on a CPU of the computing device. In some embodiments, the wirelessly controlled heat, wind, and fragrance diffuser single tower system includes a wireless data communication module with radio hardware that is configured to receive command and configuration data wirelessly from the VR software program of the VR headset. In some embodiments, the radio hardware of the wireless data communication module comprises a Bluetooth wireless data communication module. In some embodiments, the radio hardware of the wireless data communication module comprises a WiFi wireless data communication module. In some embodiments, the radio hardware of the wireless data communication module comprises both the Bluetooth wireless data communication module and the WiFi wireless data communication module. In some embodiments, the wirelessly controlled heat, wind, and fragrance diffuser single tower system includes a plurality of wireless data communication modules comprising a first wireless data communication module with radio hardware and a second wireless data communication module with radio hardware. In some embodiments, the first wireless data communication module with radio hardware comprises the Bluetooth wireless data communication module. In some embodiments, the second wireless data communication module with radio hardware comprises the WiFi wireless data communication module. In some embodiments, the wirelessly controlled heat, wind, and fragrance diffuser single tower system is wirelessly controlled by the VR software program of the VR headset used by the subject. In some embodiments, the program running on the CPU of the computing device of the single tower system receives command and configuration data from the VR software program via the VR headset and works to combine functions of the three separate devices according to the received command and configuration data to produce desired effects in nearby surroundings. In some embodiments, the touchscreen display provides visual output of configuration settings associated with the command and configuration data received from the VR software program via the VR headset. In some embodiments, the touchscreen display provides a user interface through which a user may interact with the wirelessly controlled heat, wind, and fragrance diffuser single tower system. In some embodiments, the main control board provides central connectivity to integrate all electronic components including the plurality of integrated components, the computing device and CPU, the touchscreen display, and all onboard radio hardware including the Bluetooth wireless communication module and/or the WiFi wireless data communication module. In this way, the main control board provides the main interface for each of the operational components integrated into the tower system.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments provide a wirelessly controlled heat, wind, and fragrance diffuser single tower system. In some embodiments, the wirelessly controlled heat, wind, and fragrance diffuser single tower system includes a plurality of integrated components configured to expel heat and produce wind/air flow via integrated fan (hot air and/or cool air), diffuse fragrances via fragrance diffuser, provide human interaction with the tower via integrated display, and programmatically run automated programs via a main control board, computing devices, and associated software in wireless connection with and controlled by a VR software program on a VR headset worn by a subject. In some embodiments, the VR software program runs on a processing unit of the VR headset worn by the subject user. In some other embodiments, the VR software program runs on an external processing unit. For example, the VR software program on the VR headset may run on an external GPU and CPU, on a mobile processor of a mobile device of the subject user, or on the CPU of the embedded computing device integrated into the wirelessly controlled heat, wind, and fragrance diffuser single tower system.

In some embodiments, the wirelessly controlled heat, wind, and fragrance diffuser single tower system combines the plurality of integrated components into a single tower. In some embodiments, the wirelessly controlled heat, wind, and fragrance diffuser single tower system includes a tower housing that houses and incorporates the plurality of integrated components. In some embodiments, the plurality of integrated components comprise three separate devices that are combined and integrated into the single tower (in tower housing) as an integrated system which provides cooling air from a fan, warmth from a heater, and fragrances from a fragrance diffuser.

In some embodiments, the fragrance diffuser is an aromatherapy diffuser. In some embodiments, the fragrance diffuser is a waterless oil atomizer diffuser. In some embodiments, the wirelessly controlled heat, wind, and fragrance diffuser single tower system includes a fragrance storage location in which one or more containers of fragrance or scent are stored for later use with the fragrance diffuser.

In some embodiments, the cooling fan is an oscillation cooling fan. In some embodiments, the oscillation cooling fan is configured to distribute cool air. In some embodiments, the oscillation cooling fan is configured to distribute scent and fragrances from the aromatherapy diffuser. In some embodiments, the oscillating cooling fan is configured to simultaneously distribute both the cool air and the scents and fragrances from the aromatherapy diffuser. In some embodiments, the oscillation cooling fan is configured to operate at a fan oscillation speed specified by the VR software program from among a plurality of fan oscillation speeds.

In some embodiments, the heater comprises a heating component and a heat distribution fan. In some embodiments, the heating component comprises a heating lamp. In some embodiments, the heating component comprises a heating coil. In some embodiments, the heat distribution fan is configured to operate at a heater fan speed specified by the VR software program from among a plurality of heater fan speeds.

In some embodiments, the wirelessly controlled heat, wind, and fragrance diffuser single tower system includes a main control board, a computing device, a touchscreen display, and a program which runs on a CPU of the computing device. In some embodiments, the wirelessly controlled heat, wind, and fragrance diffuser single tower system includes a wireless data communication module with radio hardware that is configured to receive command and configuration data wirelessly from the VR software program of the VR headset. In some embodiments, the radio hardware of the wireless data communication module comprises a Bluetooth wireless data communication module. In some embodiments, the radio hardware of the wireless data communication module comprises a WiFi wireless data communication module. In some embodiments, the radio hardware of the wireless data communication module comprises both the Bluetooth wireless data communication module and the WiFi wireless data communication module. In some embodiments, the wirelessly controlled heat, wind, and fragrance diffuser single tower system includes a plurality of wireless data communication modules comprising a first wireless data communication module with radio hardware and a second wireless data communication module with radio hardware. In some embodiments, the first wireless data communication module with radio hardware comprises the Bluetooth wireless data communication module. In some embodiments, the second wireless data communication module with radio hardware comprises the WiFi wireless data communication module. In some embodiments, the wirelessly controlled heat, wind, and fragrance diffuser single tower system is wirelessly controlled by the VR software program of the VR headset used by the subject. In some embodiments, the program running on the CPU of the computing device of the single tower system receives command and configuration data from the VR software program via the VR headset and works to combine functions of the three separate devices according to the received command and configuration data to produce desired effects in nearby surroundings. In some embodiments, the touchscreen display provides visual output of configuration settings associated with the command and configuration data received from the VR software program via the VR headset. In some embodiments, the touchscreen display provides a user interface through which a user may interact with the wirelessly controlled heat, wind, and fragrance diffuser single tower system. In some embodiments, the main control board provides central connectivity to integrate all electronic components including the plurality of integrated components, the computing device and CPU, the touchscreen display, and all onboard radio hardware including the Bluetooth wireless communication module and/or the WiFi wireless data communication module. In this way, the main control board provides the main interface for each of the operational components integrated into the tower system.

As stated above, the combination of aromatherapy and a controlled climate can induce a pleasurable atmosphere for relaxation and meditation. However, in order to strike the right balance between airflow and aroma, one would have to experiment with separate devices which may or may not complement each other. Also, finding a pleasurable temperature and climate for homes and dwellings is a common challenge, especially in certain spaces which may not have good circulation or air flow. Currently, fragrance diffusers typically have a single function of disbursing atomized essential oils into the air. Fans and heaters are typically separate devices, which are used independently to modify room temperatures. None of the existing devices combine all these aspects into a single system. Furthermore, these separate devices are rarely used simultaneously to create a specific, desired atmosphere. One reason this combination of devices is not used together is because it often requires too much effort from the user to properly set up and monitor the independent components. Embodiments of the wirelessly controlled heat, wind, and fragrance diffuser single tower system described in this specification solve such problems by combining separate climate control devices together into a single system to provide a pleasurable and comfortable temperature, while distributing pleasurable and complimentary aromas throughout the environment and can be programmed through wireless means to mimic or replicate certain climates and stimulate senses.

Embodiments of the wirelessly controlled heat, wind, and fragrance diffuser single tower system described in this specification differ from and improve upon currently existing options. In particular, some embodiments differ from the existing, conventional aromatherapy diffusers, fans, and heat lamps, which have long been used independently to promote holistic relaxation and comfort because currently these devices are all used separately, never as a single combined and collectively controlled system. For example, many spas use one or a combination of each of these devices to create a certain atmosphere. By contrast, the wirelessly controlled heat, wind, and fragrance diffuser single tower system described in this specification combines three specific devices into one system to generate a specific, programmed, atmospheric effect by the CPU (computing device) triggering and configuring settings of each device in connection with and wirelessly controlled by the VR software program on the VR headset of the subject.

In addition, some embodiments of the wirelessly controlled heat, wind, and fragrance diffuser single tower system improve upon the currently existing options by effectively combining these traditionally separate devices into a single functioning climate controlling and ambiance setting system. Independently, each of the separate devices-a fan, a heater, and a fragrance diffuser-work well, or work as desired. However, when trying to combine these separate devices together as a single combined system to create a specific type of environment or to create a specific mood that combines functions from each of the devices, they do not work together at all. However, the wirelessly controlled heat, wind, and fragrance diffuser single tower system of the present disclosure effectively combines these three separate devices into one system which provides cooling air from a fan, warmth from a heating lamp or a heating element, and fragrances from an aromatherapy diffuser. Moreover, these separate components are collectively controlled by external software which works to combine the elements to produce specific desired effects. Also, for purposes of overall functionality, the software of the wirelessly controlled heat, wind, and fragrance diffuser single tower system is able to independently control any single one of the three devices, independently of the others. Nevertheless, the ability to collectively control all three devices, when integrated as components of the wirelessly controlled heat, wind, and fragrance diffuser single tower system, enables greater ability to effect the local/nearby climate.

The various elements of the wirelessly controlled heat, wind, and fragrance diffuser single tower system of the present disclosure may be related in the following exemplary fashion. It is not intended to limit the scope or nature of the relationships between the various elements and the following examples are presented as illustrative examples only. In some embodiments, each of the individual devices are integrated into the wirelessly controlled heat, wind, and fragrance diffuser single tower system as components that may operate independently or, if desired, simultaneously (collectively). In some embodiments, the user can interface with the wirelessly controlled heat, wind, and fragrance diffuser single tower system by a Bluetooth connected device, a local WiFi connected device, or by way of an infrared remote control programmed to affect control of the wirelessly controlled heat, wind, and fragrance diffuser single tower system. When integrated into the wirelessly controlled heat, wind, and fragrance diffuser single tower system, the fan is separate from the heat lamp and has the ability to operate independently. In some embodiments, the user may initiate the fan program and have it oscillate if desired, independent of the other components of the wirelessly controlled heat, wind, and fragrance diffuser single tower system. In some embodiments, the waterless aromatherapy diffuser uses a misting procedure to disperse fine oil particles into the air. In some embodiments, the spray nozzle for the diffuser is positioned beneath or near the fan and angled upward, allowing the fan to blow the fragrance through the air. In some embodiments, the infrared heat lamp is separate from the fan and the aromatherapy diffuser and has the ability to operate independently. In some embodiments, the user may initiate the heat lamp using a Bluetooth connected device, a WiFi connected device or with an infrared remote control. If desired, the user may turn on all the aforementioned components simultaneously via Bluetooth control, WiFi control, and/or infrared remote control.

In some embodiments, the wirelessly controlled heat, wind, and fragrance diffuser single tower system includes a main control board that allows the user to determine which components they would like to activate (or turn on) and allows the user to specify a time duration during which the components operate. In some embodiments, the main control board has the ability to run pre-installed programs which will activate the components independently or in synchronicity. The user may also create new programs via external software or mobile application to activate the components individually or in synchronicity. In some embodiments, such external programs could be communicated to the main control board through the Bluetooth connection or the WiFi connection.

The wirelessly controlled heat, wind, and fragrance diffuser single tower system of the present disclosure generally works by the control information relayed to the wirelessly controlled heat, wind, and fragrance diffuser single tower system by a mobile device or remote control device. Thus, when a software command is wirelessly transmitted to the wirelessly controlled heat, wind, and fragrance diffuser single tower system via Bluetooth or WiFi, the main control board has a software program which processes the request and triggers the relevant components within the wirelessly controlled heat, wind, and fragrance diffuser single tower system. Depending on the main control board software program, the fan may be triggered independently, the heating element may be turned on and the fragrance diffuser may be initiated. As the software program is run on the main control board, the corresponding components will turn on or off for a specific duration of time. The main control board software program determines the order and duration for each of the components, which will create specific atmospheric conditions, desired by the user.

In some embodiments, the wirelessly controlled heat, wind, and fragrance diffuser single tower system allows for the fan to be operated entirely separately and to be programmed to oscillate in order to provide cool air. In some embodiments, the wirelessly controlled heat, wind, and fragrance diffuser single tower system allows for the heating lamp or the heating element to be operated separately to provide a direct warming sensation. In some embodiments, the wirelessly controlled heat, wind, and fragrance diffuser single tower system allows for the fragrance diffuser to be initiated, which automatically starts the fan on a low setting, in order to disburse the selected aroma throughout the room.

Additionally, the wirelessly controlled heat, wind, and fragrance diffuser single tower system of some embodiments allows for all of the components to be initiated simultaneously to create a specific, atmospheric mood. In some embodiments, the software program of the main control board is used to synchronize the components in a specific order to create the desired mood. In some embodiments, when the waterless oil diffuser is operated, the fan is automatically turned on and blows the fragrance through the air. In some embodiments, the heat lamp employs some form of safety governance to ensure it does not overheat or cause a fire hazard. In some embodiments, the main control board can turn off the heat lamp after a period of time or in the event that the temperature exceeds a safe level or a pre-designated level.

To make the wirelessly controlled heat, wind, and fragrance diffuser single tower system of the present disclosure, the system would be housed to include an oscillating fan unit, placed within a vertical shroud or tower. In some embodiments, the wirelessly controlled heat, wind, and fragrance diffuser single tower system is housed in a free-standing case or chassis which houses an oscillating fan, a heating element or heating lamp, a fragrance diffuser, and an atomizer, along with a central main control board that is used to control each of the components separately or collectively (and simultaneously). In some embodiments of the wirelessly controlled heat, wind, and fragrance diffuser single tower system, the main control board is able to run programs from external sources, via Bluetooth or WiFi connection, to create specific atmospheric moods. In some embodiments, the wirelessly controlled heat, wind, and fragrance diffuser single tower system allows a user to design custom sequences and programs to control each or all of the components integrated into the wirelessly controlled heat, wind, and fragrance diffuser single tower system.

Figure 1:
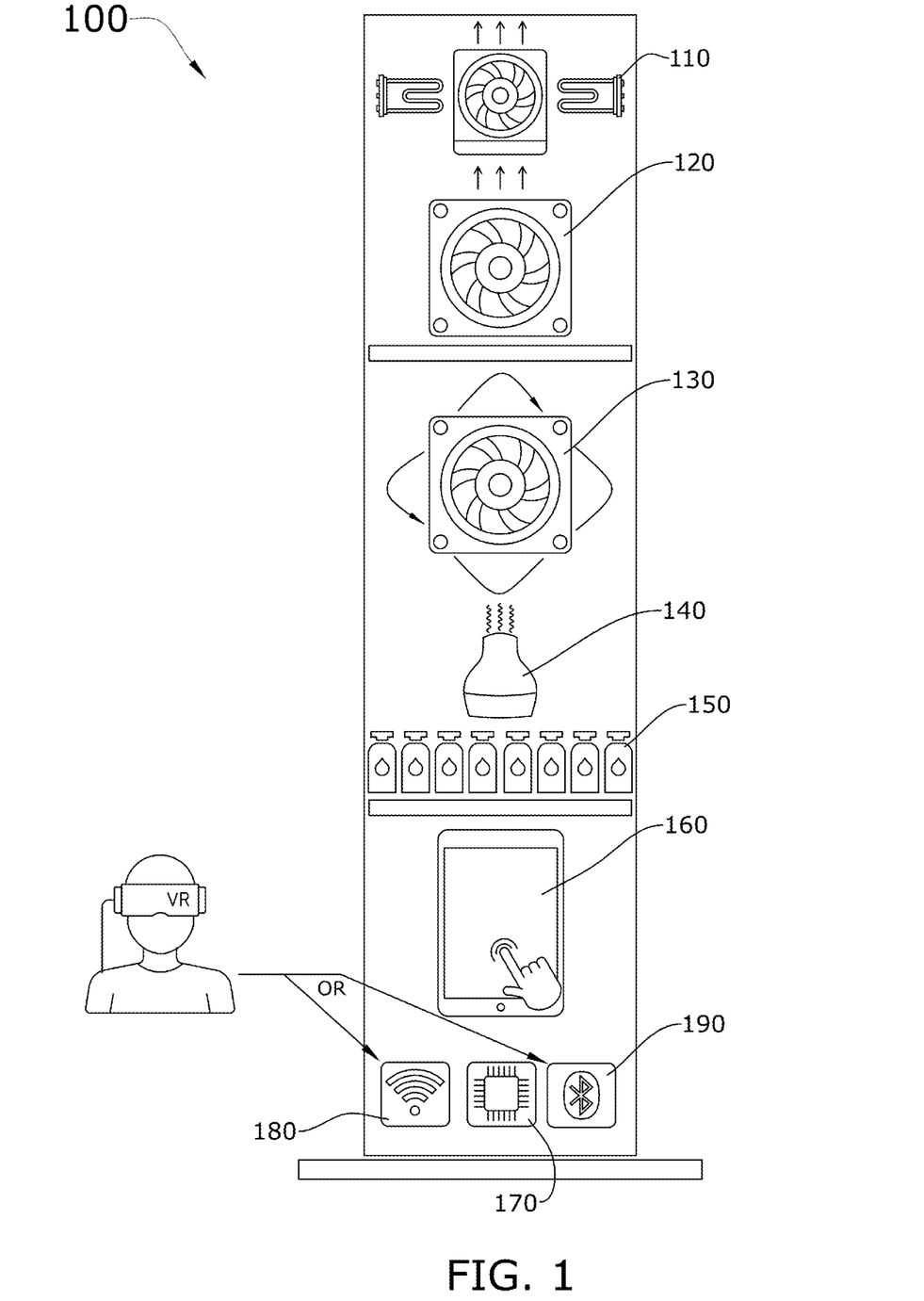
FIG. 1 conceptually illustrates a wirelessly controlled heat, wind, and fragrance diffuser single tower system in some embodiments.

By way of example, FIG. 1 conceptually illustrates a wirelessly controlled heat, wind, and fragrance diffuser single tower system 100. As shown in this figure, the wirelessly controlled heat, wind, and fragrance diffuser single tower system 100 includes several components integrated into a single tower. The several components of the wirelessly controlled heat, wind, and fragrance diffuser single tower system 100 include a heating element 110, a heat distribution fan 120, an oscillation cooling fan and scent distributor 130, a fragrance diffuser 140, a fragrance container storage location 150 with one or more containers of fragrance and/or empty containers of spent fragrance, a touchscreen display 160, a CPU of an embedded computing device 170, a WiFi wireless data communication module 180, and a Bluetooth wireless data communication module 190. Also included in the wirelessly controlled heat, wind, and fragrance diffuser single tower system 100 (but not shown in this figure) is an embedded main control board that provides a central interface for integrated tower connectivity of the heating elements 110, the heat distribution fan 120, the oscillation cooling fan and scent distributor 130, the fragrance diffuser 140, the CPU of the embedded computing device 170, the WiFi wireless data communication module 180, and the Bluetooth wireless data communication module 190 and, therefore, is a central component of the wirelessly controlled heat, wind, and fragrance diffuser single tower system 100.

In some embodiments, the heating element 110 is a heating component such as a heat lamp, a heating coil, or another heat generating component. In some embodiments, the heating elements 110 is configured to operate at a set temperature that can be adjusted according to a VR software program of a VR headset worn by a user (the subject user, as shown bottom left in this figure) and/or adjusted by direct manual input from the user. In some embodiments, the heat distribution fan 120 is configured to operate at a heater fan speed that can be adjusted according to the VR software program of the VR headset worn by the subject user and/or adjusted by direct manual input from the user.

In some embodiments, the oscillation cooling fan and scent distributor 130 operates to deliver at least cool air when initiated by the VR software program on the VR headset of the user or by direct command input by the user. In some embodiments, when the oscillation cooling fan and scent distributor 130 is initiated to deliver cool air, an option to also diffuse and distribute fragrance can be automatically selected by the VR software program of the VR headset, or manually selected by direct user input to select a fragrance to distribute along with the cool air. This works by triggering the fragrance diffuser 140 to diffuse fragrance when the option is selected. In some embodiments, when the fragrance diffuser 140 is loaded with a fragrance that is different from a particular fragrance automatically selected by the VR software program on the VR headset worn by the user or manually selected by direct user input, then an attendant or the user may retrieve the particular fragrance from the fragrance container storage location 150 if and when a container with the particular fragrance is present, and then load the fragrance diffuser 140 with the container of particular fragrance. The fragrance diffuser 140 itself may be an aromatherapy diffuser, a waterless oil atomizer diffuser, or another type of diffuser.

When user selections are optionally made available to the user (such as those options noted above), the user may select from various options that are visually output on to the touchscreen display 160 and make direct input selections of particular options as desired (e.g., by touch gesture selection on the touchscreen, by stylus input selection on the screen, etc.).

In some embodiments, the wirelessly controlled heat, wind, and fragrance diffuser single tower system 100 includes both a main control board (not shown here) and an embedded computing device 170 with a CPU. In some embodiments, the main control board is a printed circuit board (PCB) and connects to the CPU from outside of the embedded computing device 170 (e.g., by a data interface cable). In some embodiments, the main control board is an internal PCB of the embedded computing device 170.

In some embodiments, the main control board includes a plurality of connected data communication modules (or "hardware", "chips", "devices", "radios", "transceivers", etc.). In some embodiments, the connected data communication modules include at least one data communication module the supports a hard wired connection to the touchscreen display 160 to allow the user's manual input to be received by the main control board and processed by the CPU of the embedded computing device 170. In some embodiments, the connected data communication modules include at least one wireless data communication module to which the VR headset worn by the user connects to provide a data connection to the wirelessly controlled heat, wind, and fragrance diffuser single tower system 100 for the VR software program. In some embodiments, the connected data communication modules include a plurality of wireless data communication modules to allow an option for the VR software program on the VR headset to provide command and configuration data when wirelessly connected to the wirelessly controlled heat, wind, and fragrance diffuser single tower system 100. The plurality of wireless data communication modules shown in this figure include the WiFi wireless data communication module 180 and the Bluetooth wireless data communication module 190.

As such, when the user is wearing the VR headset while communicably connected to one or more of the wireless data communication modules, the wirelessly controlled heat, wind, and fragrance diffuser single tower system 100 will receive command and configuration data from the VR software program on the VR headset and be automatically triggered by the VR software program to provide the type of climate controlled and aroma controlled program as requested. For example, the VR software program could trigger the wirelessly controlled heat, wind, and fragrance diffuser single tower system 100 to replicate the sensation of lounging on a beach by emitting a coconut fragrance, which is blown into the air by the oscillation fan, while the heater provides direct heat, simulating the warmth of the sun. The careful timing and combination of these elements would be directed by the VR software program in a way that the climate and aroma sensations change at different times according to the VR software program on the VR headset worn by the user, and to do so, would simply need to send updated commands and configuration settings to the wirelessly controlled heat, wind, and fragrance diffuser single tower system 100, so that the corresponding devices of the wirelessly controlled heat, wind, and fragrance diffuser single tower system 100 can be triggered to make the changes in realtime.

In some embodiments, the fan would have the ability to oscillate in multiple directions and a range of variable speeds. In some embodiments, the fan is be controlled by the main control board. In some embodiments, the heating lamp or the heating element includes an infrared lamp, a quartz lamp, or a coil wire heating element and separately shrouded above or below the fan shroud. The heating lamp/element of some embodiments is wired and operated separately from the fan, while also being controlled by the same main control board. In some embodiments, the fragrance diffuser is a system comprised of an oil reservoir where one or multiple vials of essential oils can be stored. Each vial of oil is connected to a feeder tube which is connected to an atomizer. In some embodiments, the atomizer receives commands from the main control board which determines when it is triggered. In some embodiments, when the atomizer is triggered, the main control board sends a command to turn on the fan, if the fan is not already active, and to turn the fan setting to a low setting. In some embodiments, the main control board is also capable of triggering multiple atomizers simultaneously or independently when more than one atomizer and fragrance vial are installed.

In some embodiments, the main control board houses all of the relevant electronic components and is the main interface for each of the operational components. In some embodiments, the main control board also houses the circuitry and radios for the Bluetooth and WiFi component I/C chips. In some embodiments, the main control board also houses any CPU and memory components needed to store and run the external software program(s). In some embodiments, the main control board also includes an infrared (IR) remote module.

In some embodiments, the wirelessly controlled heat, wind, and fragrance diffuser single tower system includes an integrated IR remote sensor that receives infrared command signals from an IR remote control. In some embodiments, the IR remote sensor and the IR remote control provide an interface alternative for a user to control settings and configure programs at the tower system. In this way, a user may rely entirely or partially on the VR headset and VR software program to send commands to the tower system according to a particular program, provide direct touchscreen inputs to configure and command the devices according to user preferences for any given program, and may alternatively use the IR remote control to send commands and device configuration settings/preferences to the IR remote sensor to be received by the main control board of the tower system and processed by the CPU of the computing device to make changes to basic functions of the tower system. Examples of basic functions include, without limitation, turning the fan on or off, activating the heater or stopping the heater, starting or stopping the atomizer, separately as needed or desired. Similarly, the wirelessly controlled heat, wind, and fragrance diffuser single tower system may include other interface adaptations which would enable uses to interact with the tower to make basic changes. Such adaptations that are possible include, without limitation, hard-wired controls whereby the user can interact with the tower and make program changes or set configuration preferences via hard-wired, on-board buttons which, when pressed by the user, could provide direct input selections or which may be used in conjunction with the touchscreen display to navigate a menu or other options.

To use the wirelessly controlled heat, wind, and fragrance diffuser single tower system of the present disclosure, one may identify a place to position the wirelessly controlled heat, wind, and fragrance diffuser single tower system. For instance, the wirelessly controlled heat, wind, and fragrance diffuser single tower system may be placed in a room or at a setting where they would like to relax. The user would plug the wirelessly controlled heat, wind, and fragrance diffuser single tower system into a nearby electrical outlet and connect it to a WiFi network or pair it with a mobile device via Bluetooth. After connecting the wirelessly controlled heat, wind, and fragrance diffuser single tower system to an external mobile device or networked computer, the user would initiate a program, such as a mobile application or a computer program. The program would trigger each of the components either independently or collectively in synchronicity to create a desired atmospheric effect. For example, if the user wanted the feeling of being in a winter, snow-capped environment, the program would turn the oscillating fan on high and disperse a winter-mint fragrance. If the desired mood was a cabin with a fireplace, the heating element would be turned on and a sandalwood fragrance would be dispersed. The user would have the ability to design their own combination of moods by using the external software program.

Figure 2:
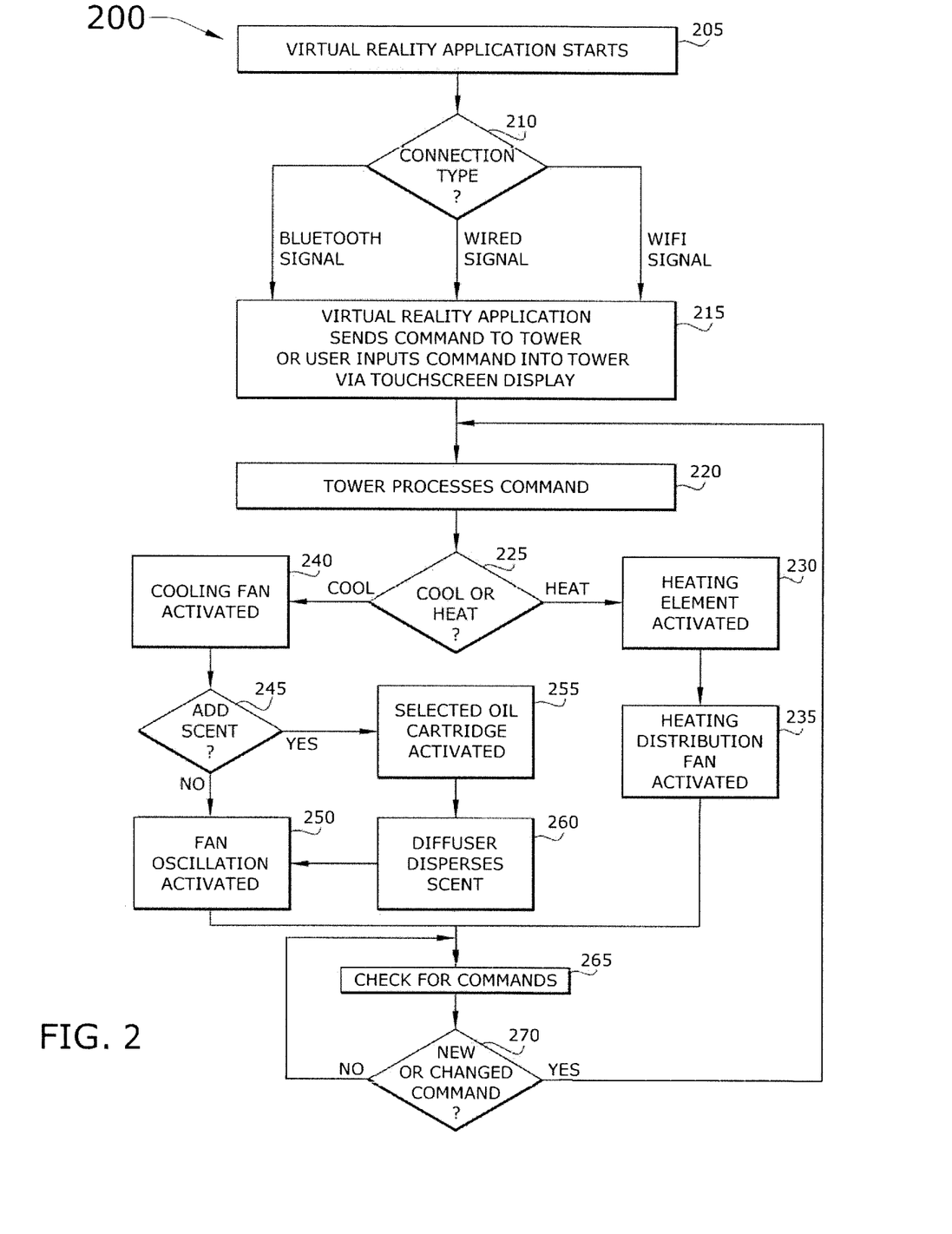
FIG. 2 conceptually illustrates a process for wirelessly controlling heat distribution, cool air flow, and fragrance diffusion by a VR program on a VR headset of a user in some embodiments.

By way of example, FIG. 2 conceptually illustrates a process for wirelessly controlling heat distribution, cool air flow, and fragrance diffusion by a VR program on a VR headset of a user 200. As shown in this figure, the process for wirelessly controlling heat distribution, cool air flow, and fragrance diffusion by a VR program on a VR headset of a user 200 starts when the VR software program starts (at 205). In some embodiments, the VR software program runs on a processing unit of the VR headset worn by the subject user. In some other embodiments, the VR software program runs on an external processing unit. For example, the VR software program on the VR headset may run on an external GPU and CPU, on a mobile processor of a mobile device of the subject user, or on the CPU of the embedded computing device integrated into the wirelessly controlled heat, wind, and fragrance diffuser single tower system. While the VR headset may provide an audio experience and a visual show or visualizations, the VR software program is typically optimized when intended to run in connection with other controllable user sensation controls, such as heat distribution, fragrance diffusion and distribution, cool air flow, etc., as provided by the wirelessly controlled heat, wind, and fragrance diffuser single tower system.

Nevertheless, in order to actual effect the nearby climate and aromas the subject user can experience, the VR headset needs to connect wirelessly to the wirelessly controlled heat, wind, and fragrance diffuser single tower system. According, the process for wirelessly controlling heat distribution, cool air flow, and fragrance diffusion 200 determines (at 210) whether the connection type is a wireless Bluetooth signal, a wireless WiFi signal, or a hard wired signal (such as may be provided with some VR headsets and/or in some displays). When the VR headset is wirelessly connected via Bluetooth or WiFi, or connected by physical wire, the process for wirelessly controlling heat distribution, cool air flow, and fragrance diffusion 200 proceeds to the next step at which the VR software program sends a command to the tower or the user inputs a command into the tower via the touchscreen display (at 215). After the tower receives the command, the process for wirelessly controlling heat distribution, cool air flow, and fragrance diffusion 200 then proceeds to the next step for the main control board and CPU of the computing device embedded into the tower system to process the command (at 220).

In some embodiments, the command is processed as one of a cool/heat option. That is, the first command may specify (in part) whether the trigger the heater or the cool air fan. Thus, the process for wirelessly controlling heat distribution, cool air flow, and fragrance diffusion 200 determines (at 225) whether the command specified a cool air option or the heat option. When the command is determined (at 225) to specify heat, the process for wirelessly controlling heat distribution, cool air flow, and fragrance diffusion 200 automatically activates (at 230) the heating element. Then the process for wirelessly controlling heat distribution, cool air flow, and fragrance diffusion 200 automatically activates the heat distribution fan (at 235). In this way, the climate in the nearby area surrounding the subject user will get warmer.

On the other hand, when the processed command is determined (at 225) to specify the cool air option, the process for wirelessly controlling heat distribution, cool air flow, and fragrance diffusion 200 of some embodiments automatically activates (at 240) the cool air fan. Then the process for wirelessly controlling heat distribution, cool air flow, and fragrance diffusion 200 determines (at 245) whether to add scent from the fragrance diffuser to the cool air. When scent is not added, the process for wirelessly controlling heat distribution, cool air flow, and fragrance diffusion 200 activates (at 250) the fan oscillation without triggering the fragrance diffuser. On the other hand, when scent is determined (at 245) to be added, then the process for wirelessly controlling heat distribution, cool air flow, and fragrance diffusion 200 activates (at 255) the selected aroma oil cartridge and activates the diffuser which disperses the scent (at 260). This is followed by activation of the fan oscillation (at 250) such that the cool air and the scent from the diffuser is distributed by the oscillating fan.

After activating the cooling and fan oscillation (with or without fragrance diffusion activated) and/or after activating the heater and heat distribution fan, the process for wirelessly controlling heat distribution, cool air flow, and fragrance diffusion 200 of some embodiments checks (at 265) for commands that may be received at the main control board and CPU of the computing device embedded in the tower system. The process for wirelessly controlling heat distribution, cool air flow, and fragrance diffusion 200 of some embodiments is programmed to check (at 265) for new or updated command and configuration options/selections at set intervals. For example, the process for wirelessly controlling heat distribution, cool air flow, and fragrance diffusion 200 may check for new or updated/changed command and configuration settings every minute, thereby ensuring that when new or updated commands and configuration settings are received at the main control board and CPU of the computing device embedded in the tower system, the new, changed, or updated commands and configuration settings are carried out by the intended devices of the tower system in near realtime as directed by the VR software program of the VR headset worn by the subject user.

In some embodiments, the process for wirelessly controlling heat distribution, cool air flow, and fragrance diffusion 200 performs this routine checking by determining (at 270) whether a new or changed/updated command or configurable setting is received. When no new or changed command or configurable setting is received, the process for wirelessly controlling heat distribution, cool air flow, and fragrance diffusion 200 simply returns to the step for checking (at 265) for new/updated commands, etc. This routine checking continues over and over again until either the VR software program on the VR headset ends (stops running) or a shutdown/power down of the tower system occurs, or until a new or updated command or configurable setting is determined (at 270) to be received, at which point the process for wirelessly controlling heat distribution, cool air flow, and fragrance diffusion 200 returns back to the step for processing the command (at 220) by the tower system. Thus, the subject user may experience a variety of sensations including heat, cool air, aromas, etc., all while enjoying either or both of visuals displayed in the VR headset and audio output from the VR headset.

Many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 3:
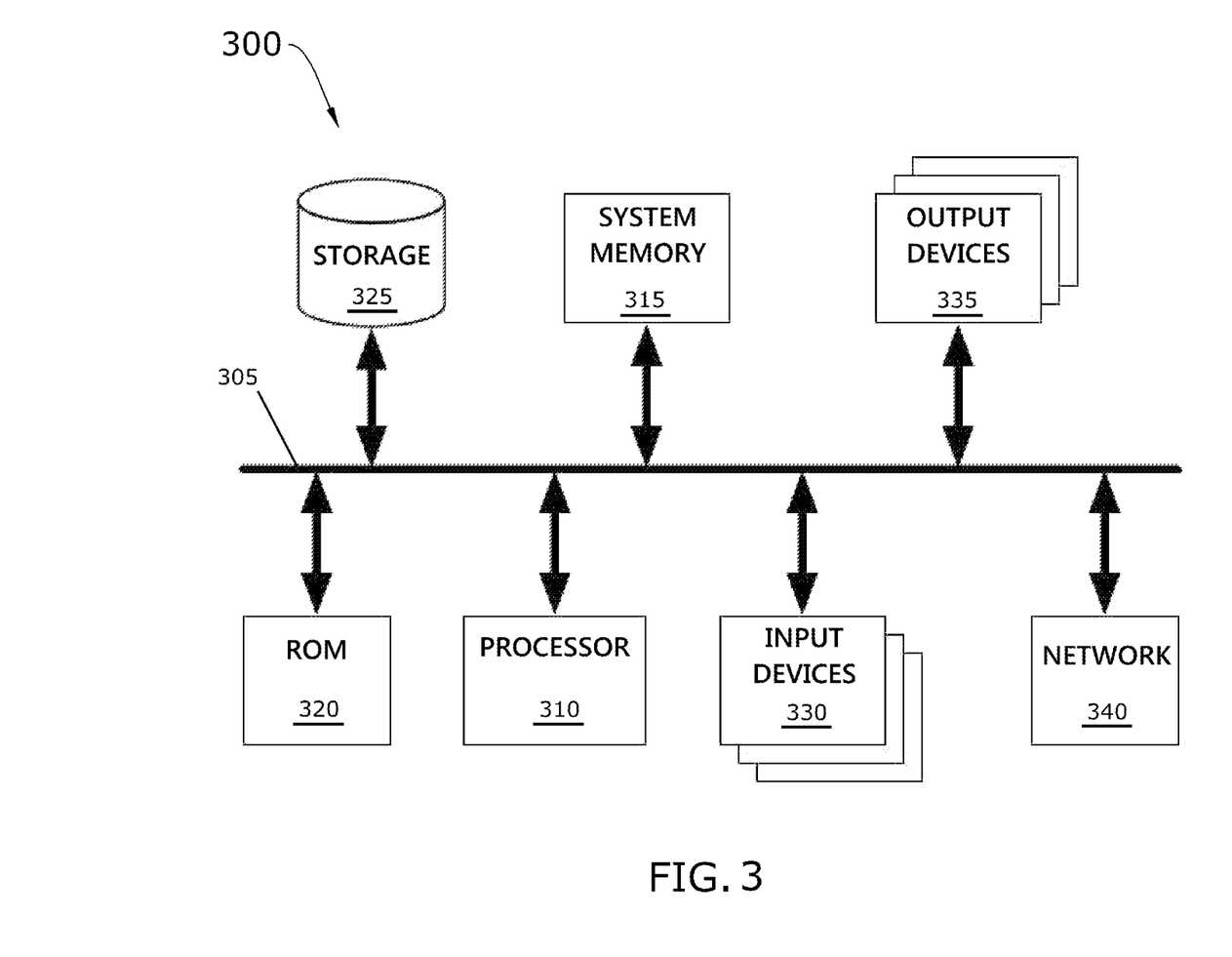
FIG. 3 conceptually illustrates an electronic system with which some embodiments of the invention are implemented.

FIG. 3 conceptually illustrates an electronic system 300 with which some embodiments of the invention are implemented. The electronic system 300 may be a computer, phone (cell phone, mobile phone, smartphone, etc.), PDA (iPod, other handheld computing device, etc.), or any other sort of electronic device or computing device. Such an electronic system includes various types of computer readable media and interfaces for various other types of computer readable media. Electronic system 300 includes a bus 305, processing unit(s) 310, a system memory 315, a read-only 320, a permanent storage device 325, input devices 330, output devices 335, and a network 340.

The bus 305 collectively represents all system, peripheral, and chipset buses that communicatively connect the numerous internal devices of the electronic system 300. For instance, the bus 305 communicatively connects the processing unit(s) 310 with the read-only 320, the system memory 315, and the permanent storage device 325.

From these various memory units, the processing unit(s) 310 retrieves instructions to execute and data to process in order to execute the processes of the invention. The processing unit(s) may be a single processor or a multi-core processor in different embodiments.

The read-only-memory (ROM) 320 stores static data and instructions that are needed by the processing unit(s) 310 and other modules of the electronic system. The permanent storage device 325, on the other hand, is a read-and-write memory device. This device is a non-volatile memory unit that stores instructions and data even when the electronic system 300 is off. Some embodiments of the invention use a mass-storage device (such as a magnetic or optical disk and its corresponding disk drive) as the permanent storage device 325.

Other embodiments use a removable storage device (such as a floppy disk or a flash drive) as the permanent storage device 325. Like the permanent storage device 325, the system memory 315 is a read-and-write memory device. However, unlike storage device 325, the system memory 315 is a volatile read-and-write memory, such as a random access memory. The system memory 315 stores some of the instructions and data that the processor needs at runtime. In some embodiments, the invention's processes are stored in the system memory 315, the permanent storage device 325, and/or the read-only 320. For example, the various memory units include instructions for processing appearance alterations of displayable characters in accordance with some embodiments. From these various memory units, the processing unit(s) 310 retrieves instructions to execute and data to process in order to execute the processes of some embodiments.

The bus 305 also connects to the input and output devices 330 and 335. The input devices enable the user to communicate information and select commands to the electronic system. The input devices 330 include alphanumeric keyboards and pointing devices (also called "cursor control devices"). The output devices 335 display images generated by the electronic system 300. The output devices 335 include printers and display devices, such as cathode ray tubes (CRT) or liquid crystal displays (LCD). Some embodiments include devices such as a touchscreen that functions as both input and output devices.

Finally, as shown in FIG. 3, bus 305 also couples electronic system 300 to a network 340 through a network adapter (not shown). In this manner, the computer can be a part of a network of computers (such as a local area network ("LAN"), a wide area network ("WAN"), or an intranet), or a network of networks (such as the Internet). Any or all components of electronic system 300 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIG. 2 conceptually illustrates a process in which the specific operations of the process may not be performed in the exact order shown and described. Specific operations may not be performed in one continuous series of operations, and different specific operations may be performed in different embodiments. Furthermore, the process could be implemented using several sub-processes, or as part of a larger macro process. Thus, one of ordinary skill in the art would understand that the invention is not to be limited by the foregoing illustrative details, but rather is to be defined by the appended claims.

I claim:

1. A wirelessly controlled heat, wind, and fragrance diffuser single tower system comprising:
   a fan shroud;
   an oscillating fan placed within the fan shroud and configured to blow air outward;
   heating elements;
   a fragrance diffuser with a spray nozzle positioned beneath the oscillating fan and angled upward to disburse fragrance up toward the oscillating fan;
   a fragrance storage area configured for placement and storage of a fragrance container with fragrance to use with the fragrance diffuser;
   a wireless data communication module comprising radio hardware configured to wirelessly receive command and configuration data that specifies a particular climate setting;
   a VR headset worn by a subject user and, when connected to the wireless data communication module, configured to (i) visually output a virtual reality environment of a VR software program in the VR headset for viewing by the subject user, (ii) receive climate selections associated with the command and configuration data that specifies the particular climate setting, and (iii) transmit the command and configuration data that specifies the particular climate setting to the wireless data communication module;
   a computing device comprising an embedded main control board and CPU, wherein the embedded main control board provides a central interface for connectivity of the heating elements, the oscillating fan, the fragrance diffuser, the CPU, and the wireless data communication module, wherein the wireless data communication module enables the computing device to (i) retrieve the command and configuration data for the particular climate setting from the wireless data communication module and (ii) operate each of the oscillating fan, the heating elements, and the fragrance diffuser according to the command and configuration data for the particular climate setting, wherein the computing device triggers activation of the heating elements and the fragrance diffuser via the central interface provided by the embedded main control board, wherein the fragrance diffuser is configured to automatically start, via the central interface provided by the embedded main control board, the oscillating fan upon activation of the fragrance diffuser by the computing device; and
   a free-standing case that houses and incorporates the oscillating fan placed within the fan shroud, the heating elements, the fragrance diffuser, the computing device, and the wireless data communication module.

2. The wirelessly controlled heat, wind, and fragrance diffuser single tower system of claim 1, wherein the fragrance diffuser comprises a waterless essential oil atomizer diffuser, wherein the embedded main control board sends a command to turn on the oscillating fan when the waterless essential oil atomizer diffuser disburses fragrance, wherein the embedded main control board starts the oscillating fan at a low setting to disburse the fragrance diffused by the waterless essential oil atomizer diffuser.

3. The wirelessly controlled heat, wind, and fragrance diffuser single tower system of claim 1, wherein the fragrance diffuser comprises an aromatherapy diffuser.

4. The wirelessly controlled heat, wind, and fragrance diffuser single tower system of claim 1, wherein the heating elements comprise a heater and a heat distribution fan.

5. The wirelessly controlled heat, wind, and fragrance diffuser single tower system of claim 4 further comprising:
   an IR remote control that externally transmits basic commands to operate the oscillating fan, the heater, the heat distribution fan, and the fragrance diffuser; and
   an IR sensor integrated into the main control board and configured to receive the basic commands from the IR remote control.

6. The wirelessly controlled heat, wind, and fragrance diffuser single tower system of claim 4, wherein the heater comprises a heating coil.

7. The wirelessly controlled heat, wind, and fragrance diffuser single tower system of claim 4, wherein the heater comprises a heat lamp.

8. The wirelessly controlled heat, wind, and fragrance diffuser single tower system of claim 7, wherein the heat lamp comprises an infrared lamp.

9. The wirelessly controlled heat, wind, and fragrance diffuser single tower system of claim 7, wherein the heater comprises a quartz lamp.

10. The wirelessly controlled heat, wind, and fragrance diffuser single tower system of claim 1, wherein the VR headset comprises wireless Bluetooth radio hardware, wherein the wireless data communication module comprises a Bluetooth wireless data communication module, wherein the radio hardware of the wireless data communication module is further configured to receive the command and configuration data as wireless Bluetooth command and configuration data from the wireless Bluetooth radio hardware of the VR headset worn by the subject user.

11. The wirelessly controlled heat, wind, and fragrance diffuser single tower system of claim 1, wherein the VR headset comprises wireless WiFi radio hardware, wherein the wireless data communication module comprises a WiFi wireless data communication module wherein the radio hardware of the wireless data communication module is further configured to receive the command and configuration data as wireless WiFi command and configuration data from the wireless WiFi radio hardware of the VR headset worn by the subject user.

12. The wirelessly controlled heat, wind, and fragrance diffuser single tower system of claim 1, wherein the oscillating fan is an oscillation cooling fan and scent distributor that is configured to distribute both cool air and fragrance diffused by the fragrance diffuser.

13. The wirelessly controlled heat, wind, and fragrance diffuser single tower system of claim 1 further comprising a touchscreen display that is configured to receive touch input from the subject user to allow the subject user to provide manual input of the command and configuration data.

14. The wirelessly controlled heat, wind, and fragrance diffuser single tower system of claim 13, wherein the embedded main control board of the computing device receives the manual input from the touchscreen display to change operation of the oscillating fan, the fragrance diffuser, and the heating elements to reproduce the particular climate setting as changed.

* * * * *